United States Patent [19]
Auweter et al.

[11] Patent Number: 5,968,251
[45] Date of Patent: Oct. 19, 1999

[54] PRODUCTION OF CAROTENOID PREPARATIONS IN THE FORM OF COLDWATER-DISPERSIBLE POWDERS, AND THE USE OF THE NOVEL CAROTENOID PREPARATIONS

[75] Inventors: Helmut Auweter, Limburgerhof; Heribert Bohn, Wattenheim; Herbert Haberkorn, Grünstadt; Dieter Horn, Heidelberg; Erik Lüddecke, Mutterstadt; Volker Rauschenberger, Ludwigshafen, all of Germany

[73] Assignee: BASF Aktiengesellschaft, Ludwigshafen, Germany

[21] Appl. No.: 08/925,061

[22] Filed: Sep. 8, 1997

[30] Foreign Application Priority Data

Sep. 9, 1996 [DE] Germany .............................. 196 375 17

[51] Int. Cl.$^6$ ....................................................... C08K 5/00
[52] U.S. Cl. ........................... 106/498; 106/407; 106/493; 106/504; 252/306; 252/311; 252/312; 426/73; 426/96; 426/98; 426/502; 426/504
[58] Field of Search ..................................... 252/311, 306, 252/312; 426/73, 540, 502, 96, 98; 106/493, 498, 407, 504

[56] References Cited

U.S. PATENT DOCUMENTS

| | | | |
|---|---|---|---|
| 3,110,598 | 11/1963 | Mueller et al. | 426/540 |
| 4,522,743 | 6/1985 | Horn et al. | 252/311 |
| 4,726,955 | 2/1988 | Horn et al. | 426/73 |
| 5,364,563 | 11/1994 | Cathrein et al. | 252/311 |

FOREIGN PATENT DOCUMENTS

| | | |
|---|---|---|
| 65 193 | 12/1985 | European Pat. Off. . |
| 410 236 | 1/1991 | European Pat. Off. . |
| 1211 911 | 9/1966 | Germany . |
| 91/06292 | 5/1991 | WIPO . |
| 94/19411 | 9/1994 | WIPO . |

OTHER PUBLICATIONS

Nutrition Reports Int., Feb. 1987, vol. 35, No. 2.
Wolever et al., Am. J. Clin Nutr 1995; 61:1241–7, (No Month).
Int. Enc. of Food and Nutrition, Bd. 9, Pergamon Press (1970) 128–31, No Month.
Chimia 21, 329 (1967), No Month.

*Primary Examiner*—Mark L. Bell
*Assistant Examiner*—Scott L. Hertzog
*Attorney, Agent, or Firm*—Keil & Weinkauf

[57] ABSTRACT

Carotenoid preparations in the form of coldwater-dispersible powders are produced by
a) preparing a molecular-disperse solution of a carotenoid, with or without an emulsifier and/or an edible oil, in a volatile, water-miscible, organic solvent at elevated temperature and adding therein an aqueous solution of a protective colloid, whereupon the hydrophilic solvent component is transferred into the aqueous phase, and the hydrophobic phase of the carotenoid results as nanodisperse phase,
b) heating the resulting hydrosol at from 40° C. to 90° C., with or without cooling of the hydrosol to from 0° C. to 30° C. beforehand, and
c) removing the solvent and the water from the heated hydrosol, and converting it into a water-dispersible dry powder.

11 Claims, 3 Drawing Sheets

18h 60°C 1) 5 min 15°C
2) 18h 60°C (B)

PRODUCTION OF CAROTENOID PREPARATIONS IN THE FORM OF COLDWATER-DISPERSIBLE POWDERS, AND THE USE OF THE NOVEL CAROTENOID PREPARATIONS

The production of carotenoid preparations in the form of coldwater-dispersible powders, and the use of the novel carotenoid preparations The invention relates to a process for producing carotenoid preparations in the form of coldwater-dispersible powders, which comprises a) preparing a molecular-disperse solution of a carotenoid, with or without an emulsifier and/or an edible oil, in a volatile, water-miscible, organic solvent at elevated temperature and adding therein an aqueous solution of a protective colloid, whereupon the hydrophilic solvent component is transferred into the aqueous phase, and the hydrophobic phase of the carotenoid results as nanodisperse phase, b) heating the resulting hydrosol at from 40° C. to 90° C. and c) removing the solvent and the water from the heated hydrosol, and converting it into a water-dispersible dry powder.

The invention furthermore relates to the novel coldwater-dispersible dry powders which contain carotenoids and are obtainable in this way and which have different color effects depending on the production variant.

Carotenoids form a group of colored pigments with a yellow to red hue which are widespread in nature and confer a characteristic color on many foodstuffs. The principal representatives of this class of substances which may be mentioned are β-carotene, β-apo-8'-carotenal, canthaxanthin and citranaxanthin. These substances, which can be prepared synthetically, represent important coloring matter, eg. as substitute for artificial dyes, both for the human and animal food industries and for pharmaceutical technology, and are of interest, for example, because of their provitamin A activity. In addition, there is increasing evidence that, for example, β-carotene is effective as a cancer prophylactic.

All carotenoids are insoluble in water, while the solubility in fats and oils is likewise found to be only low. This limited solubility, and the great sensitivity to oxidation, impede direct use of the relatively coarse-particle products obtained from the synthesis in the coloring of human and animal foods because the substances are absorbed only poorly in the coarsely crystalline form, and thus provide only poor coloring results. These disadvantageous effects for practical use of the carotenoids are particularly evident in aqueous medium because they are entirely insoluble therein.

Various processes have been described to improve the color yields and to increase the absorbability or bioavailability, all of which have the aim of reducing the size of the crystallites of the active substances to the range of particle sizes below 10 $\mu$m.

Numerous methods, inter alia described in Chimia 21, (1967) 329, WO 91/06292 and WO 94/19411, use for this purpose a colloid mill for grinding β-carotene to particle sizes of from 2 to 10 $\mu$m.

There also exist a number of combined emulsification/spray drying processes as described, for example, in DE-A-12 11 911 or in EP-A-0 410 236 (U.S. Pat. No. 5,364,563).

According to EP-B-0 065 193 (U.S. Pat. No. 4,522,743), carotenoid products in the form of fine-particle powders are produced by dissolving a carotenoid in a volatile, water-miscible organic solvent at from 50° C. to 200° C., under atmospheric or superatmospheric pressure, within less than 10 seconds. The carotenoid is precipitated from the resulting molecular-disperse solution by immediately mixing rapidly with an aqueous solution of a protective colloid at from 0° C. to 50° C. This results in a colloid-disperse β-carotene hydrosol with an orange-yellow hue. Subsequent spray drying of the dispersion provides a free-flowing dry powder which forms a clear, yellow-orange dispersion in water.

The procedure described above results in a nanoparticulate active substance dispersion which is distinguished by the depicted absorption spectrum and the resulting yellow-orange, carrot-colored hue and by an all-trans isomer content of, typically, 76%.

The requirements to be met by the finishing are particularly great for use of carotenoids in aqueous medium. It is absolutely necessary that the active substances are administered in as fine particles as possible for the required coloring and absorption properties. There is great interest in carotenoids with a wide diversity of coloring properties associated with good bioavailability.

It is an object of the invention to propose a process for producing carotenoids in the form of fine-particle powders. It was furthermore intended to provide carotenoid preparations in the form of powders with which it is possible to adjust a specific coloring effect and, moreover, achieve high bioavailability.

We have found that this object is achieved by a process for producing carotenoid preparations in the form of coldwater-dispersible powders, which comprises a) preparing a molecular-disperse solution of a carotenoid, with or without an emulsifier and/or an edible oil, in a volatile, water-miscible, organic solvent at elevated temperature and adding therein an aqueous solution of a protective colloid, whereupon the hydrophilic solvent component is transferred into the aqueous phase, and the hydrophobic phase of the carotenoid results as nanodisperse phase, b) heating the resulting hydrosol at from 40° C. to 90° C. and c) removing the solvent and the water from the heated hydrosol, and converting it into a water-dispersible dry powder.

The coldwater-dispersible dry powders comprising carotenoids which are obtainable in this way are outstandingly useful for coloring human and/or animal foods and as pharmaceutical dosage form.

Step a) in the process according to the invention can in principle be carried out as described in U.S. Pat. No. 4,522,743 (EP-A-0 065 193) by dissolving the carotenoid(s), with or without an emulsifier and/or an edible oil, in a volatile, water-miscible organic solvent at elevated temperature, eg. about 50° C. to 240° C., in particular 100° C. to 200° C., preferably 140° C. to 180° C., under atmospheric or superatmospheric pressure.

Since exposure to high temperatures may reduce the required high all-trans isomer content, the dissolution of the carotenoid(s) is carried out particularly quickly, for example in the region of seconds, eg. in 0.1 to 10 seconds, particularly preferably in less than 1 second. Superatmospheric pressure, eg. in the range from 20 bar to 80 bar, preferably 30 to 60 bar, may be advantageous for rapid preparation of the molecular-disperse solution.

The aqueous solution of a protective colloid, which is cooled where appropriate, is, immediately thereafter, added to the resulting molecular-disperse solution in such a way that the temperature of the mixture adjusts itself to about 35° C. to 80° C. During this, the hydrophilic solvent component is transferred into the aqueous phase, and the hydrophobic phase of the carotenoid(s) results as nanodisperse phase.

Figure 1:
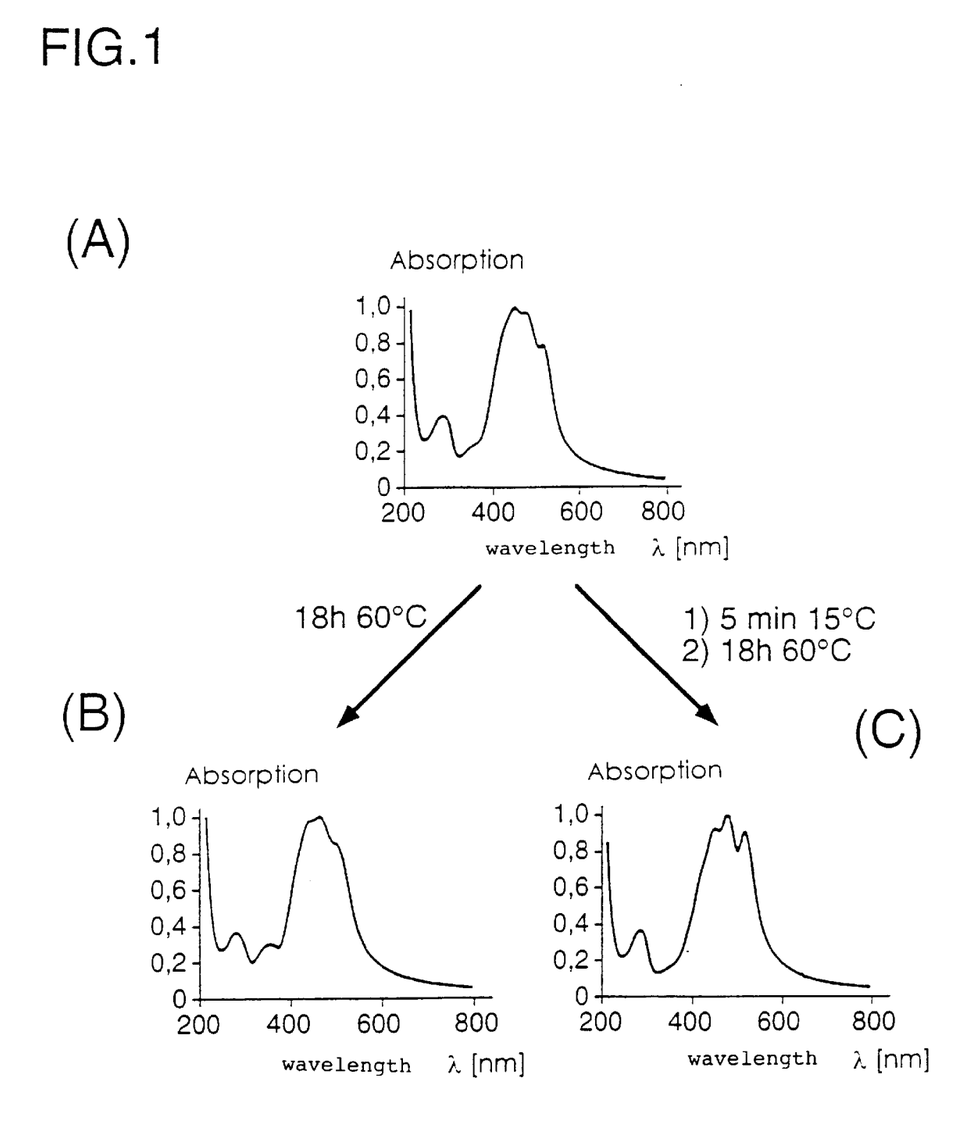
FIG. 1 is the absorption spectrum of (A) the nanoparticulate active substance dispersion produced by the procedure of U.S. Pat. No. 4,522,743; (B) the powder (A) after heating the dispersion; and (C) the powder (A) after initially cooling and then heating the dispersion.

It has now been found, surprisingly, that, as depicted in FIG. 1B, heating the carotenoid hydrosol at from 40° C. to 90° C., preferably 50° C. to 70° C., shifts the absorption to short wavelengths and thus allows hues which appear considerably yellower than those of the starting dispersion to be obtained. The cis isomerization continues further so that, for example, after heating at 60° C. for 18 hours, the content of the all-trans configuration has fallen to 60%. The time of the heating step will therefore advantageously be restricted so that at least 50% of all-trans configuration is present. The heating time is generally about 5 to 24, in particular 12 to 18, hours.

It has furthermore been found according to the invention that the degree of trans isomerization can be distinctly increased by, as shown in FIG. 1C, cooling the dispersion of active substance before the heating described above to 0 to 30° C., preferably to 10° C. to 20° C., in particular to 15° C. This cooling can advantageously take place using a heat exchanger. The duration of the cooling will depend on its capacity and the flow rate. As a rule, about 1 minute to about 5 minutes will be sufficient for the cooling, in particular in a continuous procedure. When the dispersion is subsequently heated, for example, to about 60° C., there is unexpectedly found to be reverse isomerization which even progresses beyond the original degree of isomerization to 81% of all-trans isomer. The content of cis isomer is then only 19%. This is associated with a distinct shift in the absorption spectrum into the long wavelength region. It is thus possible to obtain hues which appear considerably more orange than those of the starting dispersion.

Because of the higher all-trans content in the carotenoid dry powder, the bioavailability is higher [Jensen et al., Nutr. Rep. Int., 35, (1987) 413; Gaziano et al. Am. J. Clin. Nutr., 61, (1995) 1242] and hence the color yield from this active substance preparation is better.

The two variants of the process according to the invention result in different morphological properties of the precipitated active substance particles. Thus, the precipitated active substance particles after heating at 40° C. to 90° C., in particular 50° C. to 70° C., are essentially spherical with a diameter of, typically, 200 nm.

In the process variant in which the hydrosol is cooled to from 0° C. to 30° C. for at least 1 minute before the heating, the spherical particles are converted into elongate, prolate particles ("coffeebean structure") and, in this case, typically have a length of from 200 to 300 nm and a thickness of from 100 to 150 nm.

Figure 2:
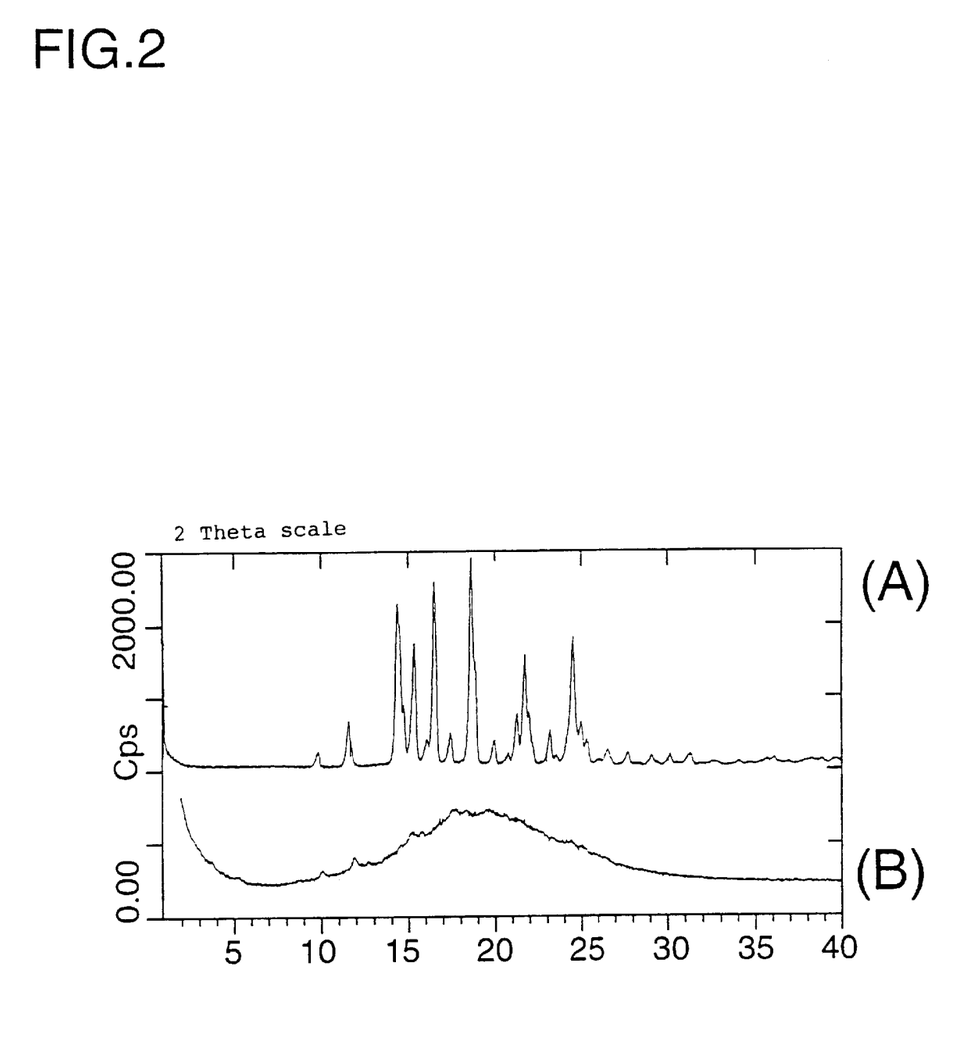
FIG. 2 is an X-ray diffraction diagram comparing (A) crystalline β-carotene and (B) the dry powder produced by the present invention.

The dry powders produced by the process variants according to the invention surprisingly show the phenomenon depicted in FIG. 2B in the X-ray diffraction diagram. Taking the example of a 20% strength β-carotene formulation, it is evident that the active substance particles are substantially X-ray amorphous, ie. the crystalline content is only about 10%. The X-ray reflections observed furthermore indicate a structure which is not identical to the crystal structure of the crystalline β-carotene whose X-ray diffraction diagram is depicted in FIG. 2A. Analyses of the X-ray spectra of the active substance particles produced according to the invention show that the spectra must be derived from a structure with more than 2 molecules in the unit cell. By contrast, the known crystal structure of β-carotene has 2 molecules in the unit cell.

In turn, a high degree of amorphism of the active substances in the dry powder suggests that the bioavailability and color yield will be higher.

The carotenoids which can be employed for carrying out the invention are the known, available, natural or synthetic representatives of this class of compounds which can be used as coloring agents, eg. β-carotene, lycopene, bixin, zeaxanthin, cryptoxanthin, citranaxanthin, lutein, canthaxanthin, astaxanthin, β-apo-4'-carotenal, β-apo-8'-carotenal, β-apo-12'-carotenal, β-apo-8'-carotenoic acid and esters of hydroxyl- and carboxyl-containing representatives of this group, eg. the low alkyl esters and, preferably, the methyl and ethyl esters.

Particularly preferably used are the representatives which have hitherto been easily obtainable industrially, such as β-carotene, canthaxanthin, astaxanthin, β-apo-8'-carotenal and β-apo-8'-carotenoic esters.

Particularly suitable for carrying out the process according to the invention are water-miscible, thermally stable, volatile solvents containing only carbon, hydrogen and oxygen, such as alcohols, ethers, esters, ketones and acetals. Ethanol, n-propanol, isopropanol, 1,2-butanediol 1-methyl ether, 1,2-propanediol 1-n-propyl ether or acetone is preferably used. It is generally expedient to use those solvents which are at least 10% miscible with water, have a boiling point below 200° C. and/or have fewer than 10 carbon atoms.

Examples of protective colloids which are used are gelatin, fish gelatin, starch, dextrin, vegetable proteins, pectin, gum arabic, casein, caseinate or mixtures thereof. However, it is also possible to employ polyvinyl alcohol, polyvinylpyrrolidone, methylcellulose, carboxymethylcellulose, hydroxypropylcellulose and alginates. For further details, reference is made to R. A. Morton, Fat Soluble Vitamins, Intern. Encyclopedia of Food and Nutrition, Vol. 9, Pergamon Press 1970, pages 128–131. To increase the mechanical stability of the final product, it is expedient to add to the colloid a plasticizer such as sugars or sugar alcohols, eg. sucrose, glucose, lactose, invert sugar, sorbitol, mannitol or glycerol.

The ratio of protective colloid and plasticizer to the carotenoid solution is generally chosen so that the final product contains from 0.5 to 20% by weight, preferably 10% by weight, of carotenoid, from 10 to 50% by weight of a protective colloid, from 20 to 70% by weight of a plasticizer, all percentages based on the dry weight of the powder, with or without small amounts of a stabilizer.

To increase the stability of the active substance against oxidative degradation, it is advantageous to add stabilizers such as α-tocopherol, butylated hydroxytoluene, butylated hydroxyanisole, ascorbic acid or ethoxyquin. They can be added either to the aqueous or to the solvent phase, but they are preferably dissolved together with the coloring agents and, with or without additional emulsifiers, in the solvent phase. Examples of emulsifiers which can be used are ascorbyl palmitate, polyglycerol fatty acid esters, sorbitan fatty acid esters, propylene glycol fatty acid esters or lecithin in a concentration of from 0 to 200%, preferably 10 to 150%, particularly preferably 20 to 80%, of the weight of the carotenoid(s).

In may also be advantageous in some circumstances additionally to dissolve in the solvent phase a physiologically acceptable oil such as sesame oil, corn oil, cottonseed oil, soybean oil or peanut oil, and esters of medium chain length vegetable fatty acids in a concentration of from 0 to 500%, preferably 10 to 300%, particularly preferably 20 to 100%, of the weight of the carotenoid(s), which is then precipitated together with the active substances and the stated additives in an extremely fine-particle form on mixing with the aqueous phase.

Depending on the nature and amount of the protective colloid used, a deep-colored viscous liquid is obtained and, in the case of a gelatinizable colloid, forms a gel-like solid. Removal of the solvent (step c) can take place in a conventional way depending on the boiling point, eg. by distillation, under atmospheric or subatmospheric pressure, or by extraction with a water-immiscible solvent. In this case, it has proven possible and expedient to employ the azeotrope which is obtained on use of isopropanol, without removing water, directly as solvent. However, removal of the solvent preferably takes place together with the removal of the water by spray drying or spray granulation.

The result is a dry powder which, on use of a water-soluble colloid, can be dissolved again in water to obtain a uniform dispersion of the active substance with particle sizes in the range below 1 μm. The active substance hydrosol obtained in this way proves to be extremely stable in a photochemical stability test, despite the fine particles.

The preparations according to the invention are, by reason of their good coldwater dispersibility, outstandingly suitable as coloring agents for food, specifically for soft drinks. They can also be added to other foodstuffs, for example baking mixtures or blancmange powders. The dry powders are furthermore suitable for producing products for supplementing human and animal food with vitamins and for producing pharmaceutical products.

Figure 3:
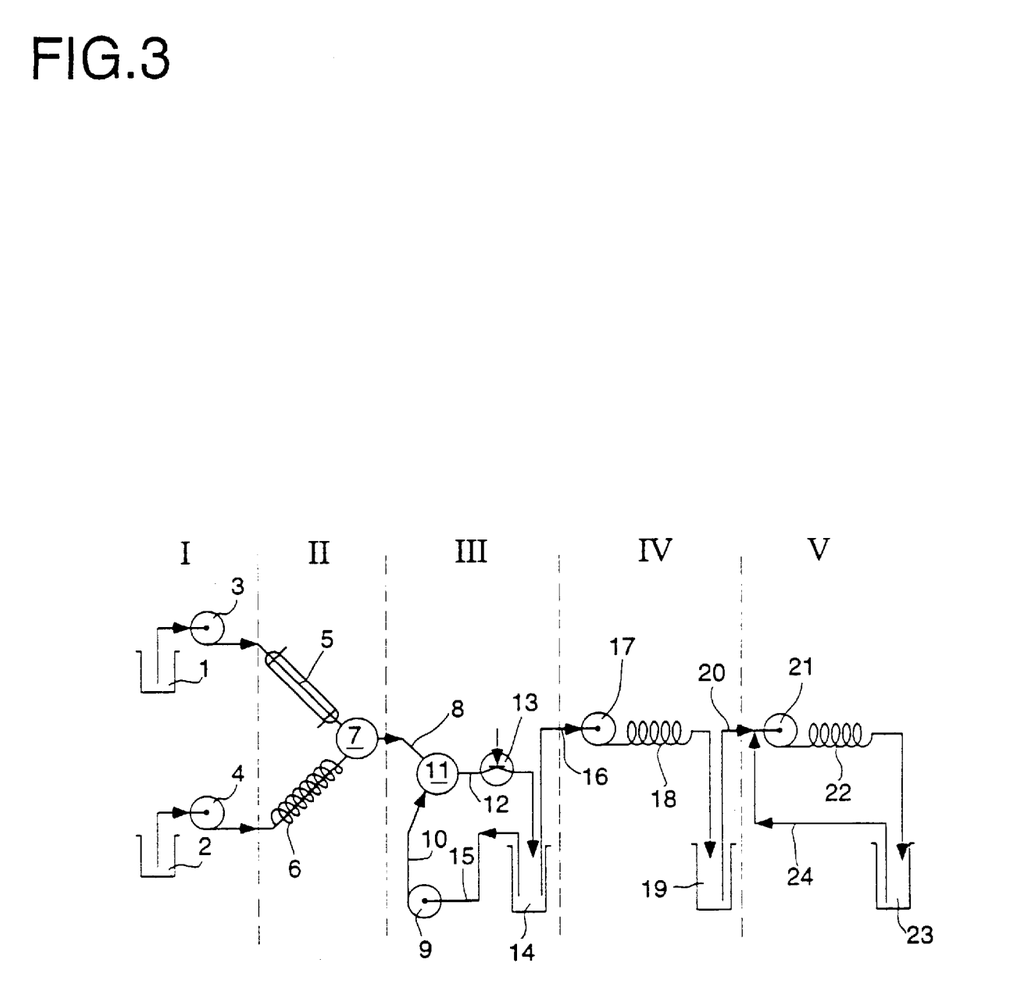
FIG. 3 is a schematic representation of an apparatus for carrying out the invention.

In detail, the process according to the invention can be carried out, for example, with an apparatus as depicted diagrammatically in FIG. 3, as follows:

The apparatus is divided into parts I to V. Part II is the high-temperature section, while the temperatures in the other parts of the apparatus are below 90° C.

A suspension of the carotenoid(s) in the selected solvent in concentrations of from 2 to 40% of the weight of the mixture, with or without addition of 0.1 to 40% by weight of stabilizers, is introduced into vessel (1). Vessel (2) contains the solvent without the carotenoid(s). The active substance suspension and the solvent are fed by pumps (3) and (4), respectively, into the mixing chamber (7), it being possible to preset the mixing ratio by choice of the particular delivery rate of the pumps and it being chosen so that the resulting carotenoid concentration in the mixing chamber is up to 10% of the weight of the solution, depending on the solvent and the residence time. The volume of the mixing chamber (7) is such that the residence time in (7) is preferably less than 1 second at the chosen delivery rate of the pumps (3) and (4).

Before entering the mixing chamber, the solvent is brought to the required temperature by the heat exchanger (6), while the active substance suspension is kept below 80° C. by feeding in through the thermally insulated feed line (5). Turbulent mixing in (7) results in the active substance dissolving at a temperature in the range from 50 to 240° C., in particular 100 to 200° C., but preferably at 140 to 180° C., and the resulting solution enters via feed line (8), after a short residence time, preferably of less than 1 second, the second mixing chamber (11) in which the active substance is precipitated in colloid-disperse form by admixing water or an aqueous protective colloid solution via pump (9) and feed line (10). The fine-particle active substance dispersion is then discharged through line (12) and through the pressure relief valve (13) and fed into the storage vessel (14). To achieve maximum concentration of active substance, the dispersion can be circulated via the suction line (15).

The active substance dispersion is conveyed from the storage vessel (14) at from 35 to 80° C., preferably from 40 to 60° C., via the pump (17), line (16) and heat exchanger (18) into the container (19). Depending on the required product quality, the active substance dispersion is either kept at 35 to 80° C., preferably at 40 to 60° C., or reduced to 0 to 30° C., preferably about 15° C., for at least 1 minute, preferably 5 minutes, in the heat exchanger (18).

The dispersion is conveyed from the container (19) via the feed line (20) and via the pump (21) through the heat exchanger (22) into the vessel (23). It is heated to, in particular, 50° C. to 70° C., preferably to about 60° C., in the heat exchanger (22). The heating time of from 5 to 24 hours, preferably 12 to 18 hours, can be achieved by circulating the dispersion through the suction line (24).

A product in powder form can be obtained from the dispersion in a conventional way, eg. as disclosed in DE-A-25 34 091 by spray drying or by spray cooling or by coating the particles, separating off and drying in a fluidized bed.

The procedure for the process according to the invention is explained in detail in the following examples.

EXAMPLE 1

63 g of β-carotene (coarsely crystalline synthetic product) and 25 g of vegetable oil were suspended in a solution of 11 g of dl-α-tocopherol and 21 g of ascorbyl palmitate in 250 g of isopropanol at 25° C. and mixed at 175° C. with 560 g of isopropanol/water (88/12) in the mixing chamber (7) (FIG. 3) with a residence time of 0.4 second. The resulting molecular-disperse solution was, immediately thereafter, fed via the feed line (8) into the mixing chamber (11) in which the β-carotene precipitated in colloid-disperse form at 45° C. by mixing with 5600 g of an aqueous gelatin solution which, besides 170 g of gelatin, contained 285 g of sugar. The entire process took place under 30 bar, adjusted by the pressure-control valve (13), in order to prevent evaporation of the solvent during the dispersing.

The colloid-disperse β-carotene dispersion obtained in the collecting vessel (14) was, without previous cooling, heated to 60° C. in the heat exchanger (22) and kept at this temperature for 18 hours, resulting in a colloid-disperse β-carotene dispersion with a yellow hue.

Spray drying the dispersion resulted in a free-flowing dry powder which forms a clear yellow dispersion in water.

EXAMPLE 2

β-Carotene was precipitated in colloid-disperse form as described in Example 1. The β-carotene dispersion obtained in the collecting vessel (14) was cooled to 15° C. in the heat exchanger (18) (FIG. 3) and thermostated at 15° C. for 15 minutes. The dispersion was then kept at 60° C. for 18 hours in the heat exchanger (22), resulting in a colloid-disperse β-carotene dispersion with an orange hue.

Spray drying of the dispersion resulted in a free-flowing dry powder which forms a clear orange dispersion in water.

We claim:

1. A process for producing carotenoid preparations in the form of coldwater-dispersible powders, which comprises
   a) preparing a molecular-disperse solution of a carotenoid, with or without an emulsifier and/or an edible oil, in a volatile, water-miscible, organic hydrophilic solvent at elevated temperature and adding therein an aqueous solution of a protective colloid, whereupon the hydrophilic solvent component is transferred into the aqueous phase, and the hydrophobic phase of the carotenoid results as nanodisperse phase,
   b) heating the resulting hydrosol at from 40° C. to 90° C. and
   c) removing the solvent and the water from the heated hydrosol, and converting it into a water-dispersible dry powder.

2. A process as claimed in claim 1, wherein the molecular-disperse carotenoid solution is prepared at from 50° C. to 240° C. and, immediately thereafter, the aqueous solution of the protective colloid is added, whereupon the temperature of the mixture adjusts itself to about 35° C. to 80° C.

3. A process as claimed in claim 1, wherein the hydrosol is, before the heating in step b), cooled to from 0° C. to 30° C.

4. A process as claimed in claim 1, wherein a molecular-disperse solution comprising the carotenoid(s) and an emulsifier in an amount of from 0 to 200% of the weight of the carotenoid(s) is prepared in step a).

5. A process as claimed in claim 1, wherein a molecular-disperse solution comprising the carotenoid(s) and an edible oil in an amount of from 0 to 500% of the weight of the carotenoid(s) is prepared in step a).

6. A carotenoid preparation in the form of a coldwater-dispersible powder, obtained by the process of claim 1.

7. A carotenoid preparation in the form of a coldwater-dispersible powder, obtained by the process of claim 1.

8. A carotenoid preparation in the form of a coldwater-dispersible powder as claimed in claim 6, wherein the X-ray amorphous content is from 70 to 100%, and wherein the remaining crystalline content has a crystal modification differing from the crystal structure of the pure carotenoid.

9. A carotenoid preparation in the form of a coldwater-dispersible powder as claimed in claim 6, which has an all-trans isomer content of at least 50%.

10. A carotenoid preparation in the form of a coldwater-dispersible powder as claimed in claim 7, which has an all-trans isomer content of at least 75%.

11. A method for improving the bioavailability of a carotenoid preparation comprising adding the powder of claim 6 to pharmaceuticals or human or animal foods.

* * * * *

UNITED STATES PATENT AND TRADEMARK OFFICE
CERTIFICATE OF CORRECTION

PATENT NO.: 5,968,251

DATED: October 19, 1999

INVENTOR(S): AUWETER et al.

It is certified that error appears in the above-identified patent and that said Letters Patent is hereby corrected as shown below:

On the cover page, item [30], "Sep. 9, 1996" should be --Sep. 13, 1996--.

Signed and Sealed this

Thirtieth Day of May, 2000

Attest:

Q. TODD DICKINSON

*Attesting Officer*　　　　*Director of Patents and Trademarks*

(12) EX PARTE REEXAMINATION CERTIFICATE (4912th)
United States Patent
Auweter et al.

(10) Number: US 5,968,251 C1
(45) Certificate Issued: Feb. 24, 2004

(54) PRODUCTION OF CAROTENOID PREPARATIONS IN THE FORM OF COLDWATER-DISPERSIBLE POWDERS, AND THE USE OF THE NOVEL CAROTENOID PREPARATIONS

(75) Inventors: Helmut Auweter, Limburgerhof (DE); Heribert Bohn, Wattenheim (DE); Herbert Haberkorn, Grünstadt (DE); Dieter Horn, Heidelberg (DE); Erik Lüddecke, Mutterstadt (DE); Volker Rauschenberger, Ludwigshafen (DE)

(73) Assignee: BASF Aktiengesellschaft, Ludwigshafen (DE)

Reexamination Request:
No. 90/006,276, May 1, 2002

Reexamination Certificate for:
Patent No.: 5,968,251
Issued: Oct. 19, 1999
Appl. No.: 08/925,061
Filed: Sep. 8, 1997

Certificate of Correction issued May 30, 2000.

(30) Foreign Application Priority Data

Sep. 13, 1996 (DE) .......................................... 196 375 17

(51) Int. Cl.$^7$ ................................................ C08K 5/00
(52) U.S. Cl. ..................... 106/498; 106/493; 106/499; 106/501.4; 106/504; 106/407; 424/489; 426/49; 426/73; 426/96; 426/98; 426/250; 426/540; 426/502; 426/504

(58) Field of Search ................................. 106/407, 493, 106/498, 499, 501.1, 504; 424/489; 426/49, 73, 96, 98, 250, 540

(56) References Cited

U.S. PATENT DOCUMENTS

| 3,655,406 A | 4/1972 | Klaui .......................... 99/148 C |
| 3,989,757 A | 11/1976 | Surmatis ....................... 260/598 |

FOREIGN PATENT DOCUMENTS

GB 918399 2/1963

*Primary Examiner*—Anthony Green (57) ABSTRACT

Carotenoid preparations in the form of coldwater-dispersible powders are produced by a) preparing a molecular-disperse solution of a carotenoid, with or wihout an emulsifier and/or an edible oil, in a volatile, water-miscible, organic solvent at elevated temperature and adding therein an aqueous solution of a protective colloid, whereupon the hydrophilic solvent component is transferred into the aqueous phase, and the hydrophobic phase of the carotenoid results as nanodisperse phase, b) heating the resulting hydrosol at from 40° C. to 90° C., with or without cooling of the hydrosol to from 0° C. to 30° C. beforehand, and c) removing the solvent and the water from the heated hydrosol, and converting it into a water-dispersible dry powder.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–5 is confirmed.

Claim 7 is cancelled.

Claims 6 and 8–10 are determined to be patentable as amended.

Claim 11, dependent on an amended claim, is determined to be patentable.

6. A carotenoid preparation in the form of a coldwater-dispersible powder, obtained by [the] *a* process [of claim 1], *which comprises*

*a) preparing a molecular-disperse solution of a carotenoid, with or without an emulsifier and/or an edible oil, in a volatile, water-miscible, organic hydrophilic solvent at elevated temperature and adding therein an aqueous solution of a protective colloid, whereupon the hydrophillic solvent component is transferred into the aqueous phase and the hydrophobic phase of the carotenoid results as a nanodisperse phase,*

*b) heating the resulting hydrosol at from 40° C. to 90° C. with a heating time of from 5 to 24 hours and*

*c) removing the solvent and the water from the heated hydrosol, and converting it into a water-dispersible dry powder.*

8. A carotenoid preparation in the form of a coldwater-dispersible powder as [claimed] *defined* in claim 6, wherein the X-ray amorphous content is from 70 to 100%, and wherein the remaining crystalline content has a crystal modification differing from the crystal structure of the pure carotenoid.

9. A carotenoid preparation in the form of a coldwater-dispersible powder as [claimed] *defined* in claim 6, which has an all-trans isomer content of at least 50%.

10. A carotenoid preparation in the form of a coldwater-dispersible powder as [claimed] *defined* in claim [7] *6*, which has an all-trans isomer content of at least 75%.

* * * * *